United States Patent [19]
Paret et al.

[11] Patent Number: 5,510,562
[45] Date of Patent: Apr. 23, 1996

[54] PROCESS FOR SEPARATING MIXTURES OF AROMATIC C8 HYDROCARBONS

[75] Inventors: Giancarlo Paret, San Donato Milanese; Renato Paludetto, Pioltello, both of Italy

[73] Assignee: Enichem S.p.A., Milan, Italy

[21] Appl. No.: 76,580

[22] Filed: Jun. 14, 1993

[30] Foreign Application Priority Data

Jun. 15, 1992 [IT] Italy .................. MI92A1462

[51] Int. Cl.$^6$ .................................. C07C 7/00
[52] U.S. Cl. ........................................ 585/805
[58] Field of Search ............................ 585/805

[56] References Cited

U.S. PATENT DOCUMENTS

| | | |
|---|---|---|
| 3,656,278 | 4/1972 | Drinkard et al. |
| 3,698,157 | 10/1972 | Allen et al. |
| 3,729,523 | 4/1973 | Grandio, Jr. et al. |
| 3,770,841 | 6/1973 | Meyers, Jr. |
| 4,585,526 | 4/1986 | Berg et al. |

FOREIGN PATENT DOCUMENTS

| | | |
|---|---|---|
| 0003662 | 8/1979 | European Pat. Off. |
| 2217300 | 9/1974 | France. |
| 1330956 | 9/1973 | United Kingdom. |
| 1354716 | 5/1974 | United Kingdom. |

Primary Examiner—Asok Pal
Assistant Examiner—Nhat D. Phan
Attorney, Agent, or Firm—Rogers & Wells

[57] ABSTRACT

A processing cycle for separating $C_8$ aromatics (mixtures of ortho-, para-, meta-xylene and ethylbenzene) is disclosed, in which a first subdivision of the mixture is preformed into two streams respectively comprising: para-xylene and ethylbenzene as the first stream; and meta- and ortho-xylene as the second stream followed by a separation of the first stream by rectification, during which ethylbenzene within specifications is obtained as the overhead fraction, with the second stream also being sent to a separation by rectification, with ortho-xylene within specifications being obtained as the bottom fraction. The possible content of $C_9$ species can be furthermore removed by subsequent distillation.

2 Claims, 3 Drawing Sheets

1 - Paraxylene-Ethylbenzene/Meta-xylene-Ortho-xylene separation
2 - Ethylbenzene distillation
3 - Para-xylene crystallization
4 - Meta-xylene/Ortho-xylene distillation 1 - Paraxylene-Ethylbenzene/
   Meta-xylene-Ortho-xylene separation
2 - Ethylbenzene distillation
3 - Para-xylene crystallization
4 - Meta-xylene/Ortho-xylene distillation 1 - Paraxylene-Ethylbenzene/
   Meta-xylene-Ortho-xylene separation
2 - Ethylbenzene distillation
3 - Para-xylene crystallization
4 - Isomerization
5 - Separation as 1

1 - Paraxylene-Ethylbenzene/
    Meta-xylene-Ortho-xylene separation
2 - Ethylbenzene distillation
3 - Para-xylene crystallization
4 - Ortho-xylene distillation
5 - Isomerization
6 - Meta-xylene distillation

PROCESS FOR SEPARATING MIXTURES OF AROMATIC C8 HYDROCARBONS

FIELD OF THE INVENTION

The present invention relates to a process for separating the constituents of a mixture of aromatic $C_8$ hydrocarbons, which substantially comprises a preliminary separation of the mixture into two streams, the first one of which contains paraxylene and ethylbenzene, and the other one is constituted by meta- and ortho-xylene, and two subsequent distinct operations of rectification during the course of which ethylbenzene is recovered as the overhead fraction, and ortho-xylene is separated as the bottom fraction.

BACKGROUND OF THE INVENTION

As is well-known, the production of aromatic hydrocarbons is greatly interested for the whole chemical industry. For that purpose, rather simple processes exist, in particular, for the purpose of separating aromatic from non-aromatic species; the resulting mixture of aromatic species is easily separated by distillation into $C_6$ aromatics (benzene) with a suitable purity for any possible use, and into $C_7$ aromatics (toluene), also with a high purity level.

The situation is completely different as regards $C_8$ aromatics, the mixtures of which not always easily be separated, because they are constituted by mixtures of isomers with very close boiling points. The most interesting $C_8$ mixture from the industrial viewpoint is that mixture which is constituted by ethylbenzene, o-xylene, p-xylene and m-xylene: as such, said mixture is used as a solvent or in gasolines, whilst much wider would be the range of possible uses of each individual isomer, if each could be separated with high purity level. So, a demand exists for high-purity para-xylene for preparing terephthalic acid and dimethyl terephthalate, intermediates for man-made fibre synthesis. Ethylbenzene, in turn, is an interesting intermediate in styrene preparation by dehydrogenation.

Usually, the processes used heretofore in order to separate the above said isomers have been mostly based on suitable combinations of superfractionation techniques and of low-temperature crystallation processes: all the above having high costs and limited yields.

According to alternative routes, the para-isomer is separated by adsorption, or by using molecular sieves: the various isomers can then be isomerized and the produced para-xylene can be separated again according to the above mentioned technique.

The ortho- and ethylbenzene isomers can also be separated by distillation.

However, the above mentioned para-isomer separation process by crystallization does not make it possible for said isomers to be totally recovered; the presence of the product in the mother liquors sent to the isomerization reduces the isomerization yield per pass, and increases the need for recycles.

Furthermore, the presence of ethylbenzene causes even more serious problems, because this produce tends to accumulate in the isomerization step, causing still more serious recycling problems. If possible, then, its conversion into dimethyl benzene always takes place with low yields and serious operation problems.

From U.S. Pat. No. 3,698,157, a process is known as well for recovering para-xylene from a mixture of $C_8$ aromatic by contacting said mixture with a suitably modified zeolite.

Also the formation is envisaged of two fractions constituted by:

| meta Pboil: | 139.12° C. | para Pboil: | 138.37° C. |
| ortho Pboil: | 144.41° C. | ethyl-b Pboil: | 136.19° C. |

Such fractions can then be separated by distillation. The meta/ortho mixture can yield the meta-isomer as the overhead fraction and the ortho-isomer as the bottom fraction, with reflux ratios of the order of 10–20, and with a number of trays comprises within the range of from 150 to 200.

The para/ethyl-b mixture can also be separated by distillation, under burdensome conditions (however, obviously, not as burdensome as they would be if the whole stream were submitted to distillation).

DETAILED DESCRIPTION OF THE INVENTION

Figure 1:
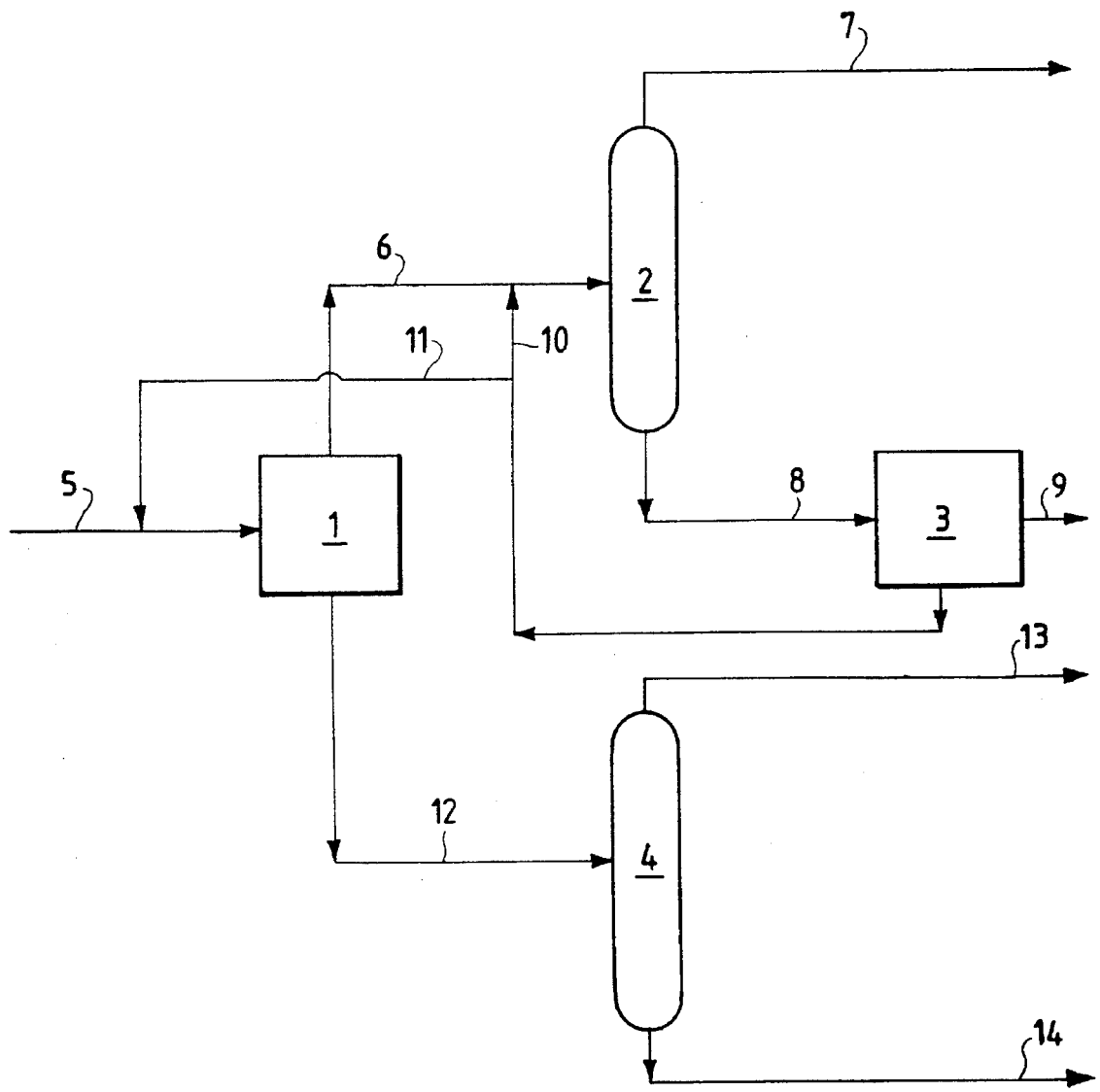
FIG. 1 shows the scheme used in Example 1.

The present Applicants have found now that the four isomers of the mixture of $C_8$ aromatics can be separated in a simple and cheap way by adopting a processing cycle which substantially comprises a preliminary separation of said mixture into two streams, and subsequent rectification operations.

The composition of a typical mixture of the interesting isomer can be represented as follows:

| | |
|---|---|
| ethylbenzene | 20 |
| para-xylene | 20 |
| meta-xylene | 40 |
| ortho-xylene | 20 |

In the first step of the cycle followed in the process according to the present invention, the mixture is sent to a separation zone containing a suitable agent, in which zone para-xylene and ethylbenzene are separated from the other binary mixture consisting of ortho- and meta-xylene.

This separation can be carried out by using well known means for those skilled in the art, such as, e.g., those disclosed in the above mentioned U.S. Pat. No. 3,698,157, or in U.S. Pat. No. 3,656,278.

The ethylbenzene and para-xylene-containing stream is then sent to a rectification column operating with a reflux ratio within the range of from 50 to 80, and containing from 300 to 400 trays.

Ethylbenzene within specifications and paraxylene are obtained as the overhead and bottom fractions, respectively.

The latter may also contain 1 to 10% by weight of other isomers: in such a case, a further purification will be carried out by crystallization, and the mother liquors will be recycled.

The parallel ortho-xylene and meta-xylene mixture is sent, in turn, to a rectification column in which said isomers are separated at respective purity levels higher than 99%: ortho-xylene as the bottom fraction, and meta-xylene as the overhead fraction, both of the them being obtained with practically quantitative yields relative to the feedstock.

In the ortho-xylene fraction impurities constituted by $C_9$ species can still be present, which will simply be distilled off. Should the production of meta- and ortho-isomers not be interesting, the mixture can suitably be sent to an isomerization step: in such a case, the operating cycle according to the present invention will produce only ethylbenzene and para-xylene with purity levels within specification, because the effluent stream form the isomerization zone will also be fed to a separation step on-line with the initial separation step.

Also the isomerization, if present, is carried out according to well-known techniques for those skilled in the art.

The rectification column for ortho-xylene/metaxylene mixture operates, according to the cycle according to the present invention, with a reflux ratio within the range of from 10 to 20, with a number of trays comprised within the range of from 150 to 200.

The cycle according to the present invention will be better understood by referred to the accompanying figures to which reference is made in the following examples, which are supplied solely for the purpose of better explaining the invention without limiting the scope of protection thereof.

EXAMPLE 1

Separation of $C_8$ Mixture Without Isomerization

The feedstock composition approximately corresponds to the composition of $C_8$ aromatics deriving from a reformed gasoline.

With reference to FIG. 1, such a feed stock stream (5) is separation in the separation unit 1 into two streams, of which stream (6) contained EB+PX and stream (12) only contains MX and OX.

Stream (6) is distilled in unit 2, yielding EB as the overhead within purity specification (7). The bottom may contain a residual amount of EB, so stream (8) is treated by crystallization, yielding PX within specifications (9), and the mother liquors (10/11) are recycled.

The second stream (12), containing MX and OX, can be treated by distillation, yielding an MX stream (13) and an OX stream (14), both of them being within specification.

A typical material balance can be as follows:

|    | 5  | 6  | 7  | 8  | 9  | 10 | 11 | 12 | 13 | 14 |
|----|----|----|----|----|----|----|----|----|----|----|
| EB | 20 | 20 | 20 | 3  | —  | 3  | —  | —  | —  | —  |
| MX | 40 | —  | —  | —  | —  | —  | —  | 40 | 40 | —  |
| PX | 20 | 20 | —  | 23 | 20 | 3  | —  | —  | —  | —  |
| OX | 20 | —  | —  | —  | —  | —  | —  | 20 | —  | 20 |

Streams (7) and (14) can be within specification even if the MX-OX and PX-EB separation (1) is not complete; stream (13) can be within specifications only if the feed to column (4) (stream 12) contained EB and PX within specification limits. The crystallization mother liquors are recycled to column 2 if they are free from MX and OX (stream 10), otherwise they are added to the feedstock stream (5).

EXAMPLE 2

The same feedstock is taken into consideration and the production of EB and PX is carried out with MX and OX being completely isomerized.

Figure 2:
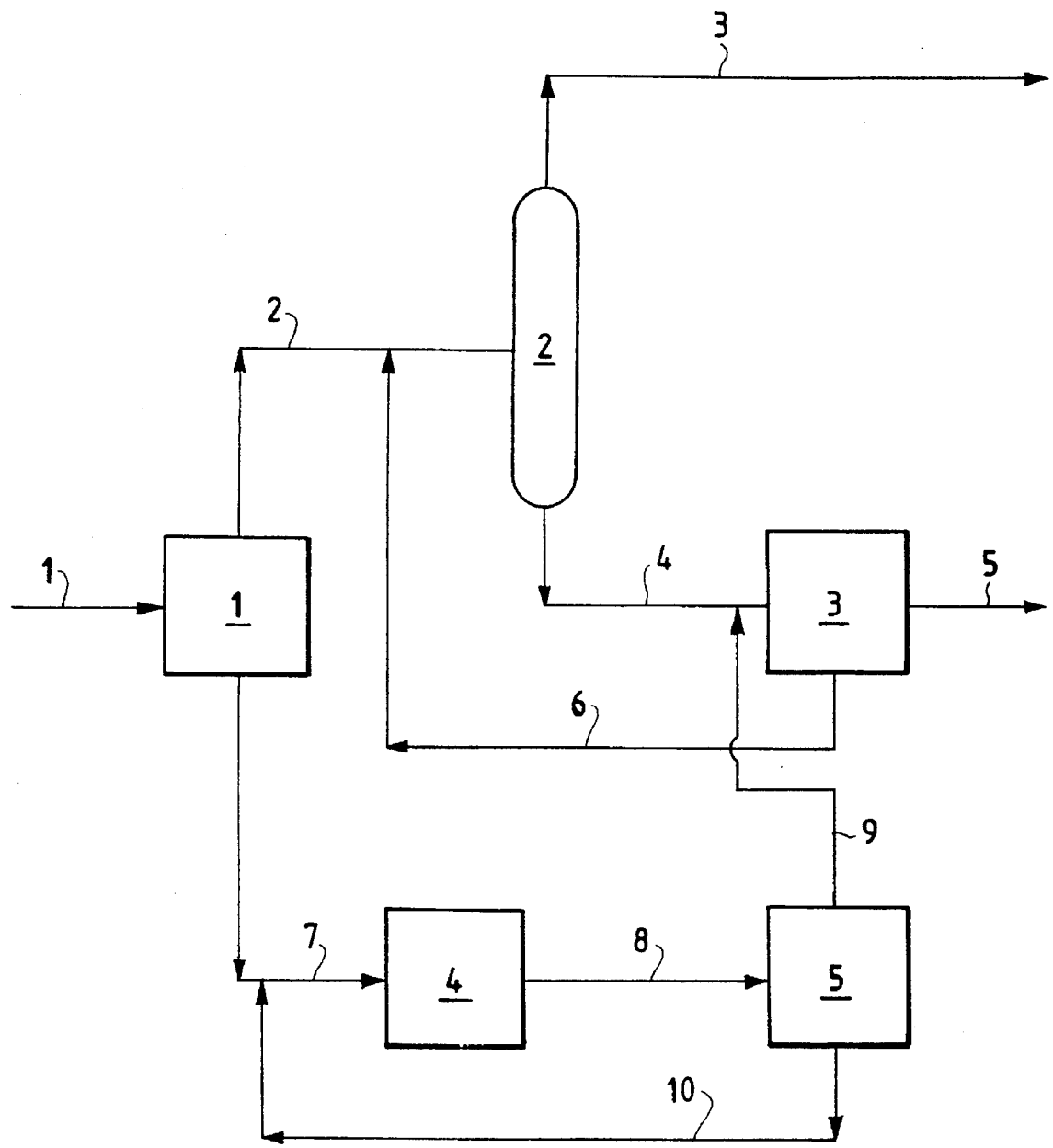
FIG. 2 shows the scheme used in Example 2.

According to the scheme of FIG. 2, the feedstock stream is fed to the separation unit 1 and from there the PX+EB stream is sent to EB separation, carried out in column 2 by distillation; the bottom stream, constituted by PX and small amounts of EB, is fed to a PX purification by crystallization 3, and crystallization mother liquors are recycled upstream, to distillation 2 if they are free from MX and OX, or, otherwise, to separation 1.

MX-OX stream, which may contain PX and EB, is sent to the isomerization 4 and from there to a separation (5) analogous to 1, from which the formed PX is sent to purification 3; the residual portion, essentially constituted by MX and OX, is recycled to isomerization 4.

In such a way, only PX and EB are produced; no rigid specifications exist for the MX-OX stream.

This scheme makes it possible, if desired, for OX or MX within specifications to be produced by adding a distillation column for distilling the MX+OX effluent from 5 or 1, with the residual stream being recycled.

In this case, the material balance is as follows:

|    | 1  | 2  | 3  | 4  | 5  | 6  | 7   | 8   | 9  | 10  |
|----|----|----|----|----|----|----|-----|-----|----|-----|
| EB | 20 | 20 | 20 | 5  | —  | 5  | —   | —   | —  | —   |
| PX | 20 | 20 | —  | 30 | 80 | 20 | —   | 60  | 60 | —   |
| MX | 40 | —  | —  | —  | —  | —  | 160 | 120 | —  | 120 |
| OX | 20 | —  | —  | —  | —  | —  | 80  | 60  | —  | 60  |

EXAMPLE 3

Figure 3:
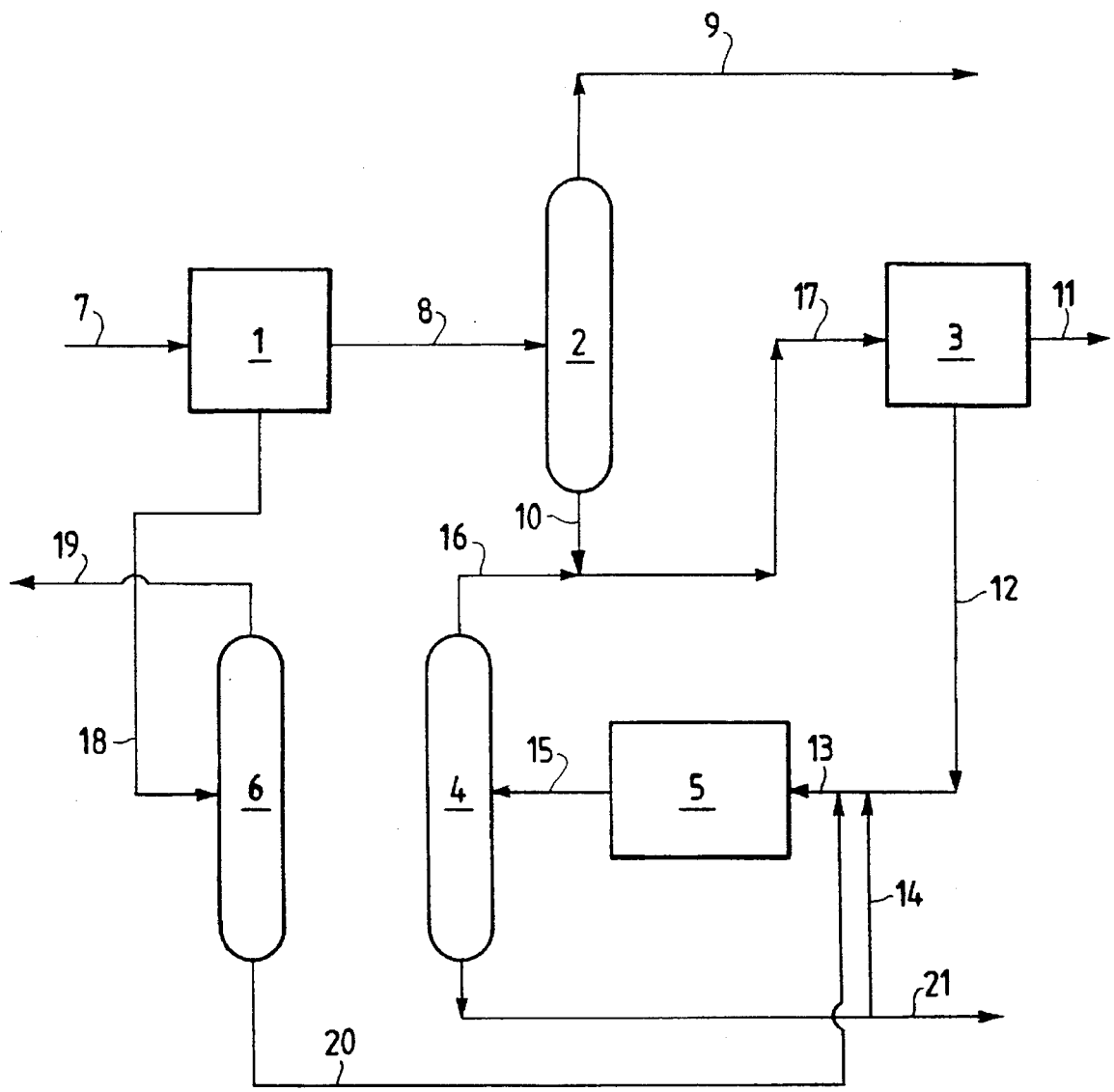
FIG. 3 shows the scheme used in Example 3.

A more general example which makes it possible all for the isomers to be obtained within specifications and, within certain limits, for the production mix to be varied regarding the isomeric xylene species (PX, OX and MX) is based on the scheme reported in FIG. 3.

Such a scheme makes it possible for the process to be operated according to different configurations.

For all of said configurations, the production of EB is limited to the amount contained in the feedstock and by the recovery capacity of column 2. The column 6 yields the desired amount of MX according to overhead specifications, with the bottom stream being destined to isomerization 5.

The isomerization processes the bottom stream from distillation 6 together with the crystallization mother liquors. A loss of EB due to dealkylation may occur. The column 4 can separation, at its bottom, OX within specifications from $C_8$'s, or, still, as its bottom stream, an OX-rich stream can be obtained, with the subsequent crystallization 3 being relieved by increasing PX concentration.

Crystallization 3, which may be a multi-step one, makes it possible for PX coming from distillation 2 to be purified by removing any residual EB, which is left in the mother liquors, and is sent to isomerization.

An exemplifying material balance may be as follows:

| Run for producing all of the isomers, within specifications: from 100 kg of feedstock, the production of 17 kg of EB, 50 kg of PX, 10 kg of OX, 20 kg of MX (3 kg of EB to loss) is expected | | | | | | | | | | | | | | | |
|---|---|---|---|---|---|---|---|---|---|---|---|---|---|---|---|
|    | 7  | 8  | 9  | 10 | 11 | 12  | 13  | 14 | 15  | 16  | 17  | 18 | 19 | 20 | 21 |
| EB | 20 | 20 | 17 | 3  | —  | 6   | 6   | —  | 3   | 3   | 6   | —  | —  | —  | —  |
| PX | 20 | 20 | —  | 20 | 50 | 20  | 20  | —  | 50  | 50  | 70  | —  | —  | —  | —  |
| MX | 40 | —  | —  | —  | —  | 100 | 120 | —  | 100 | 100 | 100 | 40 | 20 | 20 | —  |
| OX | 20 | —  | —  | —  | —  | 40  | 60  | —  | 50  | 40  | 40  | 20 | —  | 20 | 10 |

We claim:

1. A process for separately isolating each of para-xylene, ethylbenzene meta-xylene, and ortho-xylene from a mixture of $C_8$ aromatic hydrocarbons containing same, which comprises the following steps:

(a) separating the mixture by suitable means into a first stream containing a para-xylene/ethylbenzene mixture, and a second stream containing a meta=xylene/ortho-xylene mixture;

(b) rectifying the para-xylene/ethylbenzene mixture into an overhead fraction consisting essentially of ethylbenzene and a bottom fraction comprising para-xylene, so as to separately isolate ethylbenzene;

(c) rectifying the meta-xylene/ortho-xylene mixture into an overhead fraction consisting essentially of meta-xylene and a bottom fraction consisting essentially of a mixture of meta-xylene and ortho-xylene, so as to separately isolate meta-xylene;

(d) purifying the bottom fraction of step (b) by crystallization in order to obtain para-xylene and mother liquor, so as to separately isolate para-xylene;

(e) subjecting the bottom fraction of step (c) and the mother liquor of step (d) to isomerization; and (f) distilling effluent from the isomerization of step (e) in order to yield a bottom stream consisting essentially of ortho-xylene, so as to separately isolate ortho-xylene.

2. The process of claim 1, further comprising the step of recycling to isomerization the bottom stream of step (f).

* * * * *